(12) United States Patent
Hill et al.

(10) Patent No.: US 10,500,356 B2
(45) Date of Patent: Dec. 10, 2019

(54) SYSTEM AND METHOD FOR CONTROLLING INSUFFLATION PRESSURE DURING INEXSUFFLATION

(71) Applicant: KONINKLIJKE PHILIPS N.V., Eindhoven (NL)

(72) Inventors: Peter Douglas Hill, Monroeville, PA (US); Seunghyun Lee, Murrysville, PA (US); April Stewart Nathan, Pittsburgh, PA (US)

(73) Assignee: Koninklijke Philips N.V., Eindhoven (NL)

( * ) Notice: Subject to any disclaimer, the term of this patent is extended or adjusted under 35 U.S.C. 154(b) by 771 days.

(21) Appl. No.: 14/386,462

(22) PCT Filed: Mar. 19, 2013

(86) PCT No.: PCT/IB2013/052170
§ 371 (c)(1),
(2) Date: Sep. 19, 2014

(87) PCT Pub. No.: WO2013/140333
PCT Pub. Date: Sep. 26, 2013

(65) Prior Publication Data
US 2015/0059753 A1    Mar. 5, 2015

Related U.S. Application Data

(60) Provisional application No. 61/613,702, filed on Mar. 21, 2012.

(51) Int. Cl.
*A61M 16/00* (2006.01)
*A61M 16/16* (2006.01)

(52) U.S. Cl.
CPC ........ *A61M 16/0003* (2014.02); *A61M 16/00* (2013.01); *A61M 16/0009* (2014.02);
(Continued)

(58) Field of Classification Search
CPC .......... A61M 16/0003; A61M 16/0009; A61M 16/161; A61M 16/00; A61M 2205/3317; A61M 2016/0036
See application file for complete search history.

(56) References Cited

U.S. PATENT DOCUMENTS 3,961,627 A    6/1976   Ernst
5,540,220 A    7/1996   Gropper et al.
(Continued)

FOREIGN PATENT DOCUMENTS

CN    101874734 A    11/2010
GB      1312799 A     4/1973
(Continued)

*Primary Examiner* — Tan-Uyen T Ho
*Assistant Examiner* — Margaret M Luarca
(74) *Attorney, Agent, or Firm* — Michael W. Haas

(57) ABSTRACT

The present disclosure pertains to a system and method for controlling insufflation pressure during inexsufflation of a subject. The system inexsufflates the subject such that tidal flow and/or tidal volume are monitored during insufflation, and insufflation pressure is adjusted to maintain the flow rate of the pressurized flow of breathable gas until a target tidal volume is reached for the insufflation. When the target tidal volume has substantially been reached, the system is causes gas to be evacuated from the airway of the subject. This may provide for more precise, customized therapy for the subject than is provided by conventional inexsufflation systems in which inspiratory flow may not be monitored and/or controlled. In one embodiment, the system comprises one or more of a pressure generator, a subject interface, one or more sensors, a processor, a user interface, electronic storage, and/or other components.

15 Claims, 4 Drawing Sheets

(52) U.S. Cl.
CPC ... *A61M 16/161* (2014.02); *A61M 2016/0027* (2013.01); *A61M 2016/0033* (2013.01); *A61M 2016/0036* (2013.01); *A61M 2205/3303* (2013.01); *A61M 2205/3317* (2013.01); *A61M 2205/3365* (2013.01); *A61M 2205/3379* (2013.01)

(56) References Cited

U.S. PATENT DOCUMENTS

| | | | |
|---|---|---|---|
| 8,776,792 B2* | 7/2014 | Milne | A61M 16/00 128/204.18 |
| 2002/0020410 A1* | 2/2002 | Rydin | A61M 16/0051 128/200.24 |
| 2005/0039749 A1* | 2/2005 | Emerson | A61M 16/0006 128/204.23 |
| 2007/0199566 A1 | 8/2007 | Be'Eri | |
| 2008/0283060 A1* | 11/2008 | Bassin | A61M 16/0051 128/204.18 |
| 2010/0180897 A1* | 7/2010 | Malgouyres | A61M 16/00 128/204.23 |
| 2010/0275921 A1 | 11/2010 | Schindhelm | |
| 2012/0272961 A1* | 11/2012 | Masic | A61M 16/0051 128/204.23 |
| 2014/0116441 A1* | 5/2014 | McDaniel | A61M 16/0051 128/204.23 |

FOREIGN PATENT DOCUMENTS

| | | |
|---|---|---|
| NO | WO2011000359 A1 | 1/2011 |
| WO | WO2007054829 A2 | 5/2007 |
| WO | WO2010058308 A2 | 5/2010 |
| WO | WO2011045735 A1 | 4/2011 |

* cited by examiner

SYSTEM AND METHOD FOR CONTROLLING INSUFFLATION PRESSURE DURING INEXSUFFLATION

CROSS-REFERENCE TO RELATED APPLICATIONS

This patent application claims the priority benefit under 35 U.S.C. § 371 of international patent application No. PCT/IB2013/051722, filed Mar. 5, 2013, which claims the priority benefit under 35 U.S.C. § 119(e) of U.S. Provisional Application No. 61/613,702 filed on Mar. 21, 2012, the contents of which are herein incorporated by reference.

BACKGROUND OF THE INVENTION

1. Field of the Invention

The present disclosure pertains to a system and method for controlling insufflation pressure during inexsufflation of a subject.

2. Description of the Related Art

Coughing functions to clear mucus from the airway of a subject. During a cough, inhaled air is drawn in slowly (<1 LPS). Then, the glottis closes and the expiratory muscles contract, increasing the subglottic pressure. The cough begins when the glottis opens and air is forced quickly from the lungs. The lungs continue to empty at a rate of roughly 4 LPS until the lungs are sufficiently decompressed. Some people, due to injury, disease, or thoracic surgery, find it difficult or impossible to cough effectively on their own. For these people, assisted, or artificial, airway clearance is prescribed.

Artificial airway clearance can be achieved via many methods. One such method employs the use of a mechanical in-exsufflator (MI-E). An MI-E is a medical device that delivers positive airway pressure through the mouth, nose, or a tracheostomy, gently filling the lungs to capacity (insufflation). It then abruptly reverses pressure which generates an expiratory flow, mimicking a cough (exsufflation).

In conventional systems, determining inexsufflation settings for a particular patient can be imprecise and/or inaccurate. Each patient has unique respiratory characteristics (e.g. airway resistance, lung compliance, patient effort, etc.), which can change over time and/or during the course of treatment. Usually, relying on past experience, and through trial and error, a physician may arrive at inexsufflation settings that may or may not be optimal.

SUMMARY OF THE INVENTION

Accordingly, one or more aspects of the present disclosure relate to a system configured to inexsufflate a subject. In some embodiments, the system comprises a pressure generator, one or more sensors and/or one or more processors. In some embodiments, the one or more processors comprise a target module and a control module. The pressure generator is configured to generate and control delivery of a pressurized flow of breathable gas to an airway of the subject. The one or more sensors are configured to generate output signals conveying information related to one or more gas parameters of the pressurized flow of breathable gas. The one or more processors are configured to execute computer program modules. The target module is configured to obtain a target tidal flow rate and a target tidal volume, to determine when the target tidal volume has been reached during an individual insufflation based on the output signals, to monitor the tidal flow rate based on the output signals, and to compare the monitored tidal flow rate with the target tidal flow rate. The control module is configured to control the pressure generator, based on the output signals, to control an insufflation pressure of the pressurized flow of breathable gas during an insufflation of the subject to maintain the flow rate of the pressurized flow of breathable gas substantially at the target tidal flow rate until the target tidal volume is reached for the insufflation, wherein, responsive to a determination by the target module that the target tidal volume has substantially been reached, the control module is configured to control the pressure generator to cause the gas to be evacuated from the airway of the subject.

Yet another aspect of the present disclosure relates to a method of inexsufflating a subject. In some embodiments, the method comprises generating and controlling delivery of a pressurized flow of breathable gas to an airway of the subject; generating output signals conveying information related to one or more gas parameters of the pressurized flow of breathable gas; obtaining a target tidal flow rate and a target tidal volume, determining when the target tidal volume has been reached during an individual insufflation based on the output signals, monitoring the tidal flow rate based on the output signals, and comparing the monitored tidal flow rate with the target tidal flow rate; controlling, based on the output signals, an insufflation pressure of the pressurized flow of breathable gas during an insufflation of the subject to maintain the flow rate of the pressurized flow of breathable gas substantially at the target tidal flow rate until the target tidal volume is reached for the insufflation; and responsive to a determination that the target tidal volume has substantially been reached, causing the gas to be evacuated from the airway of the subject.

Still another aspect of the present disclosure relates to a system configured to inexsufflate a subject. In some embodiments, the system comprises means for generating and controlling delivery of a pressurized flow of breathable gas to the airway of the subject, means for generating output signals conveying information related to one or more gas parameters of the pressurized flow of breathable gas, and means for executing computer program modules. In some embodiments, the computer program modules comprise means for obtaining a target tidal flow rate and a target tidal volume, determining when the target tidal volume has been reached during an individual insufflation based on the output signals, monitoring the tidal flow rate based on the output signals, and comparing the monitored tidal flow rate with the target tidal flow rate, and means for controlling, based on the output signals, the means for generating and controlling delivery of a pressurized flow of breathable gas to control an insufflation pressure of the pressurized flow of breathable gas during an insufflation of the subject to maintain the flow rate of the pressurized flow of breathable gas substantially at the target tidal flow rate until the target tidal volume is reached for the insufflation. Responsive to a determination that the target tidal volume has substantially been reached, the means for controlling the means for generating and controlling delivery of a pressurized flow of breathable gas to control the insufflation pressure is configured to control the means for generating and controlling delivery of a pressurized flow of breathable gas to evacuate the gas from the airway of the subject.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
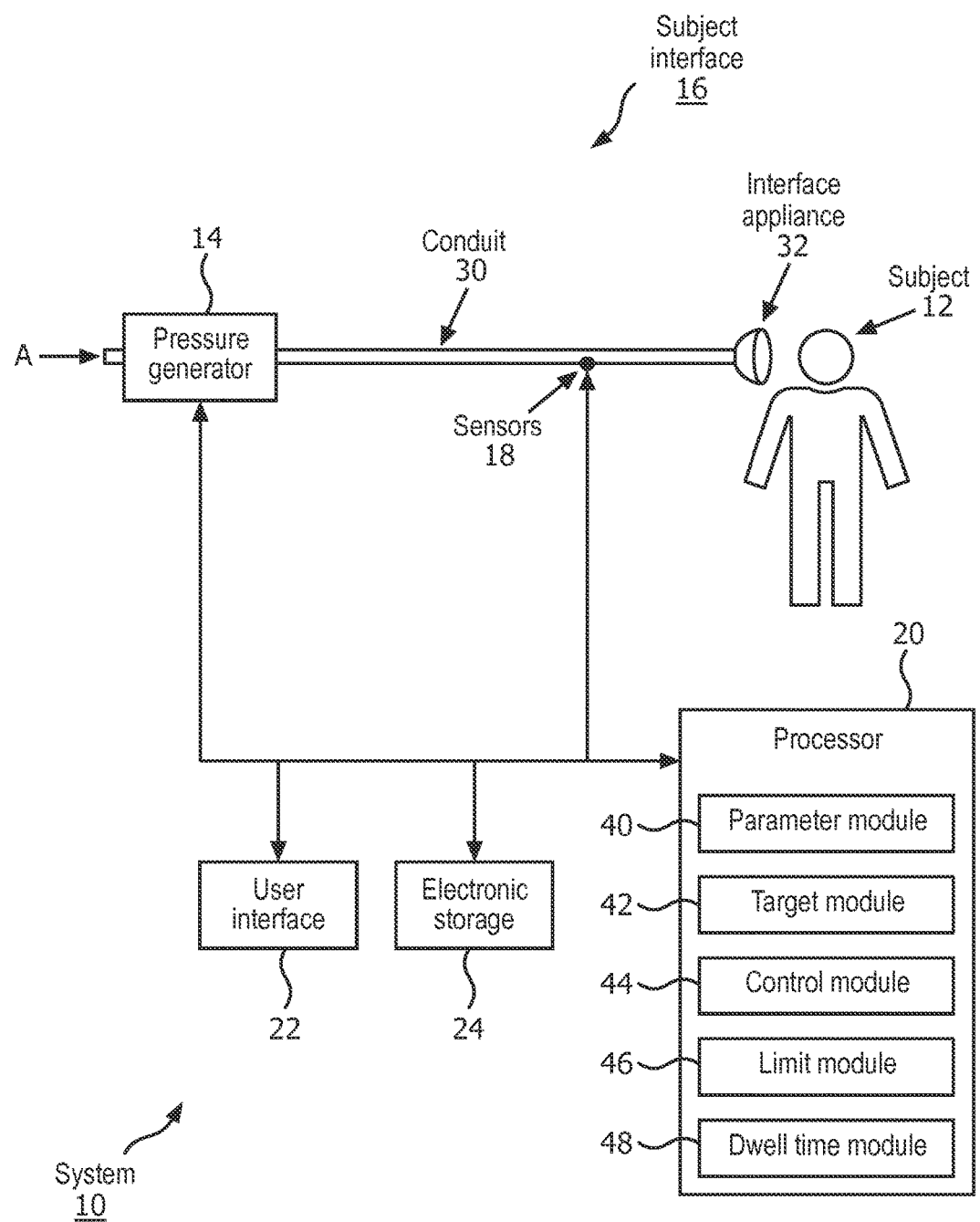
FIG. 1 schematically illustrates a system configured to insufflate and exsufflate a subject.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates a system 10 configured to insufflate and exsufflate (hereafter "inexsufflate") a subject 12. In particular, system 10 inexsufflates subject 12 such that tidal flow and/or tidal volume are monitored during insufflation, and insufflation pressure is adjusted to maintain the flow rate of the pressurized flow of breathable gas until a target tidal volume is reached for the insufflation. Responsive to the determination that the target tidal volume has been reached, system 10 is configured to evacuate the gas from the airway of subject 12. This may provide for more precise, customized therapy for subject 12 than is provided by conventional inexsufflation systems in which inspiratory flow may not be monitored and/or controlled. In one embodiment, system 10 comprises one or more of a pressure generator 14, a subject interface 16, one or more sensors 18, a processor 20, a user interface 22, electronic storage 24, and/or other components.

Pressure generator 14 is configured to provide a pressurized flow of breathable gas for delivery to the airway of subject 12 (inflow to subject 12) and/or to draw gas from the airway (outflow from subject 12) of subject 12 (e.g., to exsufflate). Pressure generator 14 may be configured such that one or more gas parameters of the pressurized flow of breathable gas are controlled in accordance with a therapy regime to inexsufflate subject 12. The one or more gas parameters may include, for example, one or more of flow, pressure, humidity, velocity, acceleration, and/or other parameters. In some embodiments, pressure generator 14 is a device dedicated to mechanical inexsufflation. In some embodiments, pressure generator 14 is a ventilator and/or positive airway pressure device configured to provide therapy other than and/or in addition to inexsufflation.

Pressure generator 14 receives a flow of gas from a gas source, such as the ambient atmosphere, as indicated by arrow A and elevates the pressure of that gas for delivery to the airway of a patient. Pressure generator 14 is any device, such as, for example, a pump, blower, piston, or bellows, that is capable of elevating the pressure of the received gas for delivery to a patient. The present disclosure also contemplates that gas other than ambient atmospheric air may be introduced into system 10 for delivery to the patient. In such embodiments, a pressurized canister or tank of gas containing air, oxygen, and/or another gas may supply the intake of pressure generator 14.

Pressure generator 14 may comprise one or more valves for controlling the pressure and/or flow direction of gas in pressure generator 14, a manifold defining the gas flow path in pressure generator 14, and/or other components. The present disclosure also contemplates controlling the operating speed of the blower, for example, either alone or in combination with such valves and/or the manifold, to control the pressure/flow of gas provided to and/or drawn from the patient.

By way of a non-limiting example, pressure generator 14 may be configured to adjust the parameters of the pressurized flow of breathable gas in accordance with an inexsufflation therapy regime. In one embodiment, the therapy regime may dictate that the pressurized flow of breathable gas is delivered to the airway of subject 12 at a first pressure level during insufflation. The first pressure level is sufficiently high that the lungs of subject 12 are at least partially filled during insufflation. After insufflation, pressure generator 14 may reduce the pressure of the pressurized flow of breathable gas with sufficient abruptness that expiratory flow through the airway of subject 12 is sufficient to remove mucus and/or other debris from the airway and/or lungs of subject 12. The pressure may be reduced from the first pressure level to a second pressure level that is substantially lower than the first pressure level. The second pressure level may, for example, be a negative pressure, below atmospheric pressure. After expiration is complete, pressure generator 14 may return the pressure of the pressurized flow of breathable gas to the first pressure level to facilitate another inspiration in preparation for another inexsufflation. After a series of inexsufflations, inexsufflation may be ceased.

Subject interface 16 is configured to deliver the pressurized flow of breathable gas to the airway of subject 12. As such, subject interface 16 comprises conduit 30, interface appliance 32, and/or other components. Conduit 30 is configured to convey the pressurized flow of gas to interface appliance 32. Conduit 30 may be a flexible length of hose, or other conduit, that places interface appliance 32 in fluid communication with pressure generator 14. Interface appliance 32 is configured to deliver the flow of gas to the airway of subject 12. In some embodiments, pressure generator 14 is a dedicated inexsufflation device and interface appliance 32 is configured to be removably coupled with another interface appliance being used to deliver respiratory therapy to subject 12.

In some embodiments, interface appliance 32 is invasive. Some examples of invasive interface appliances that may comprise interface appliance 32 are endotracheal tubes, tracheostomy tubes, and or other devices. In some embodiments, interface appliance 32 is non-invasive. As such, interface appliance 32 non-invasively engages subject 12. Non-invasive engagement comprises removably engaging an area (or areas) surrounding one or more external orifices of the airway of subject 12 (e.g., nostrils and/or mouth) to communicate gas between the airway of subject 12 and interface appliance 32. Some examples of non-invasive interface appliance 32 may comprise, for example, a nasal cannula, a nasal mask, a nasal/oral mask, a full face mask, a total face mask, or other interface appliances that communicate a flow of gas with an airway of a subject. The present disclosure is not limited to these examples, and contemplates delivery of the flow of gas to the subject using any interface appliance.

Although subject interface 16 is illustrated in FIG. 1 as a single-limbed interface for the delivery of the flow of gas to the airway of the subject, this is not intended to be limiting. The scope of this disclosure comprises double-limbed circuits having a first limb configured to both provide the flow of gas to the airway of the subject, and a second limb configured to selectively exhaust gas (e.g., to exhaust exhaled gases).

Sensors 18 are configured to generate output signals conveying information related to one or more gas parameters of the gas within subject interface 16. The one or more gas parameters comprise flow, volume, pressure, a composition (e.g., concentration(s) of one or more constituents), temperature, humidity, acceleration, velocity, acoustics, changes in a parameter indicative of respiration, and/or other gas parameters.

In one embodiment, sensors 18 include a flow rate sensor and/or a pressure sensor. Sensors 18 may comprise one or more sensors that measure such parameters directly (e.g., through fluid communication with the flow of gas in subject interface 16). Sensors 18 may comprise one or more sensors that generate output signals related to one or more parameters of the flow of gas indirectly. For example, one or more of sensors 18 may generate an output based on an operating parameter of pressure generator 14 (e.g., a valve driver or motor current, voltage, rotational velocity, and/or other operating parameters), and/or other sensors. Although gas parameter sensors 18 are illustrated at a single location within (or in communication with) conduit 30 between interface appliance 32 and pressure generator 14, this is not intended to be limiting. Sensors 18 may include sensors disposed in a plurality of locations, such as for example, within pressure generator 14, within (or in communication with) interface appliance 32, and/or other locations.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some implementations, processor 20 may comprise a plurality of processing units. These processing units may be physically located within the same device (e.g., pressure generator 14), or processor 20 may represent processing functionality of a plurality of devices operating in coordination.

As shown in FIG. 1, processor 20 is configured to execute one or more computer program modules. The one or more computer program modules may comprise one or more of a parameter module 40, a target module 42, a control module 44, a limit module 46, a dwell time module 48, and/or other modules. Processor 20 may be configured to execute modules 40, 42, 44, 46, and/or 48 by software; hardware; firmware; some combination of software, hardware, and/or firmware; and/or other mechanisms for configuring processing capabilities on processor 20.

It should be appreciated that although modules 40, 42, 44, 46, and/or 48 are illustrated in FIG. 1 as being co-located within a single processing unit, in implementations in which processor 20 comprises multiple processing units, one or more of modules 40, 42, 44, 46, and/or 48 may be located remotely from the other modules. The description of the functionality provided by the different modules 40, 42, 44, 46, and/or 48 described below is for illustrative purposes, and is not intended to be limiting, as any of modules 40, 42, 44, 46, and/or 48 may provide more or less functionality than is described. For example, one or more of modules 40, 42, 44, 46, and/or 48 may be eliminated, and some or all of its functionality may be provided by other modules 40, 42, 44, 46, and/or 48. As another example, processor 20 may be configured to execute one or more additional modules that may perform some or all of the functionality attributed below to one of modules 40, 42, 44, 46, and/or 48.

Parameter module 40 is configured to determine one or more parameters within system 10. The one or more parameters within system 10 may comprise gas parameters related to the pressurized flow of breathable gas, breathing parameters related to respiration of subject 12, and/or other parameters. Parameter module 40 is configured to determine the one or more parameters based on the output signals of sensors 18. The information determined by parameter module 40 may be used for determining a target insufflation tidal flow rate, a target insufflation tidal volume, controlling pressure generator 14, determining a pressure limit, determining a dwell time, and/or for other uses.

Target module 42 is configured to obtain a target tidal flow rate and/or a target tidal volume (flow multiplied by time) for an insufflation. The target tidal flow and/or target tidal volume may be obtained at manufacture, obtained by target module 42 from information entered by a user via user interface 22, obtained from information related to previous respiration by subject 12 from sensors 18 and/or parameter module 40, and/or obtained by another method.

Target module 42 is configured to determine the tidal flow rate and compare the determined tidal flow rate to the target tidal flow rate. Target module 42 is configured to determine the tidal flow rate and compare the tidal flow rate to the target tidal flow rate based on one or more of output signals from sensors 18, based on information from parameter module 40, and/or based on other information. Target module 42 is configured to determine the tidal flow rate and compare the tidal flow rate to the target tidal flow rate at one or more time points and/or continuously during an individual insufflation. By way of a non-limiting example, the tidal flow rate determinations made by target module 42 may be used by control module 44 to control pressure generator 14 to make small pressure adjustments over time to maintain the target tidal flow rate.

Target module 42 is configured to determine when the target tidal volume has been reached during an individual insufflation based on one or more of output signals from sensors 18, based on information from parameter module 40, and/or based on other information. In some embodiments, target module 42 is configured to determine total insufflation volume (flow integrated over time) at one or more time points, and/or continuously during an individual insufflation. Responsive to the total insufflation volume equaling and/or exceeding the target tidal volume obtained by target module 42, target module 42 determines that the target tidal volume has been reached for that insufflation. By way of a non-limiting example, the information related to the determination by target module 42 that the target tidal volume has been reached for an individual insufflation may be used by control module 44 to control pressure generator 14 to begin exsufflation of subject 12.

Control module 44 is configured to control pressure generator 14 to adjust the insufflation pressure of the pressurized flow of breathable gas during an insufflation of subject 12. Control module 44 controls pressure generator 14 from a starting insufflation pressure to maintain the flow rate of the pressurized flow of breathable gas at the target tidal flow rate until the target tidal volume is reached for the insufflation. Control module 44 is configured to control pressure generator 14 based on the output signals from sensors 18, based on information from parameter module 40, based on information from target module 42, and/or based on other information. Such control may be feedback control. Responsive to a determination by target module 42 that the target tidal volume has been reached for an insufflation, the control module is configured to control pressure generator 14 to cause the gas to be evacuated from the airway of subject 12.

Figure 2:
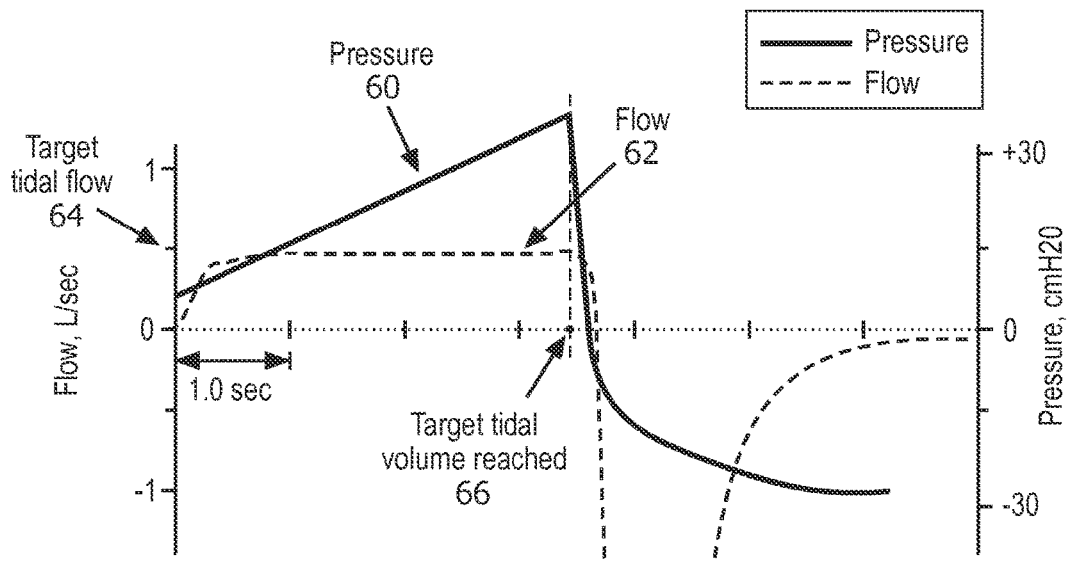
FIG. 2 is a graphical representation of insufflation pressure control during insufflation of a subject.

By way of a non-limiting example, FIG. 2 is a graphical representation (flow/pressure versus time) of insufflation pressure control during inexsufflation of a subject. The pressure 60 is steadily increased to maintain the flow 62 at the target tidal flow 64 until the target tidal volume is reached 66. When target tidal volume 66 is reached, pressure 60 is decreased to cause the gas to be evacuated from the airway of the subject.

Returning to FIG. 1, in some embodiments, control module 44 is configured to control pressure generator 14 to generate the flow of gas in accordance with a ventilator and/or positive airway pressure therapy regime instead of, and/or in addition to, the mechanical inexsufflation regime described above. By way of non-limiting example, processor 20 may control pressure generator 14 such that the pressure support provided to the subject via the flow of gas comprises non-invasive ventilation, positive airway pressure support, continuous positive airway pressure support, bi-level support, BiPAP®, and/or other types of pressure support therapy. In this example, subject 12 may trigger pressure generator 14 to switch from an airway pressure support operation regime to the mechanical inexsufflation operation regime and/or to switch from the mechanical inexsufflation operation regime to the airway pressure support regime. Subject 12 may trigger the switch from one operation regime to the other via user interface 22, and/or by other methods.

Limit module 46 is configured to obtain an insufflation pressure limit and/or to determine when the insufflation pressure limit is reached. The insufflation pressure limit may be obtained at manufacture, obtained by limit module 46 from information entered by a user via user interface 22, obtained from information generated by parameter module 40, obtained from information related to previous respiration by subject 12, and/or by other methods. In some embodiments, limit module 46 may obtain an insufflation pressure limit from a range of possible insufflation pressure limits. The upper and lower ends of the possible insufflation pressure limit range may be set by a user via user interface 22 and/or by other methods. By way of a non-limiting example, the upper end of the possible pressure limit range may be set at 70 cmH$_2$O and/or the lower end of the possible pressure limit range may be set at 10 cmH$_2$O.

In some embodiments, control module 44 is configured to control pressure generator 14 to maintain the insufflation pressure at the pressure limit, without regard for tidal flow. Control module 44 is configured to control pressure generator 14 to maintain the insufflation pressure at the pressure limit responsive to a determination by limit module 46 that the insufflation pressure limit has been reached. Control module 44 is configured to control pressure generator 14 to maintain the pressure at the pressure limit until the target tidal volume is reached, until the flow rate increases above the target flow rate (thus requiring a feedback controlled insufflation pressure decrease below the pressure limit), and/or control module 44 determines the target tidal volume is not reached in a predetermined amount of time.

The predetermined amount of time may be obtained at manufacture, obtained by limit module 46 from information entered by a user via user interface 22, obtained from information generated by parameter module 40, obtained from information related to previous respiration by subject 12, and/or by other methods. The predetermined amount of time is a length of time configured to maximize the inspired tidal volume while limiting discomfort and/or other physical issues experienced by subject 12 while insufflation continues. The predetermined amount of time may be lengthened and/or shortened during an insufflation based on lung compliance of subject 12, the maximum insufflation pressure, the flow rate, and/or other factors. At the conclusion of the predetermined amount of time, control module 44 is configured to control pressure generator 14 to cause the gas to be evacuated from the airway of subject 12.

In some embodiments, control module 44 is configured to control pressure generator 14 to maintain the insufflation pressure at or above a pressure minimum. The insufflation pressure minimum may be obtained at manufacture, obtained by limit module 46 from information entered by a user via user interface 22 (e.g. pressure minimum information entered by subject 12, a doctor, a decision maker, and/or other users) obtained from information generated by parameter module 40, obtained from information related to previous respiration by subject 12, and/or by other methods.

Figure 3:
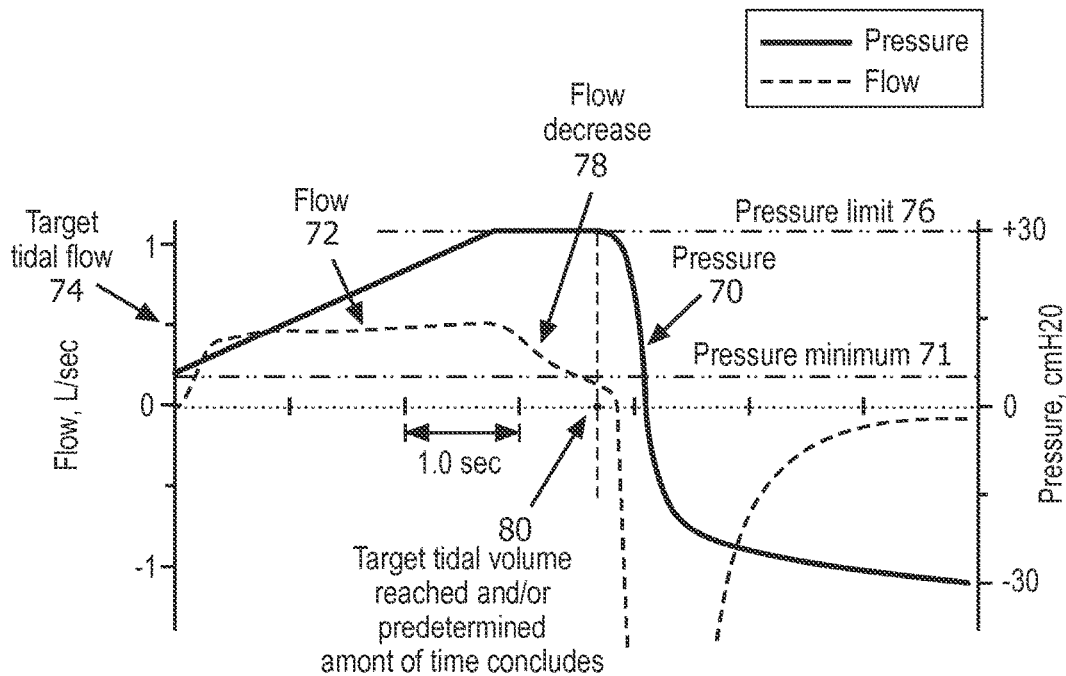
FIG. 3 is a graphical illustration of insufflation pressure control at an insufflation pressure maximum during inhalation of a subject.

By way of a non-limiting example, FIG. 3 is a graphical illustration (pressure/flow versus time) of insufflation pressure control at an insufflation pressure maximum during inhalation of a subject. The pressure 70 is steadily increased above the pressure minimum 71 to maintain the flow 72 at the target tidal flow 74 until the pressure upper limit is reached 76. Pressure 70 is maintained at pressure limit 76 even as flow 72 decreases 78 until the target tidal volume is reached, and/or the conclusion of a predetermined amount of time 80.

Returning to FIG. 1, dwell time module 48 is configured to obtain a dwell time. The dwell time may be obtained at manufacture, obtained by dwell time module 48 from information entered by a user via user interface 22, obtained from information generated by parameter module 40, obtained from information related to previous respiration by subject 12, and/or by other methods. In some embodiments, control module 44 is configured to control pressure generator 14 to conclude insufflation (adjust pressure so flow rate is at or near zero) and maintain the target tidal volume of pressurized breathable gas in the airway of subject 12 for the dwell time obtained by dwell time module 48. At the conclusion of the dwell time, control module 44 is configured to control pressure generator 14 to cause the gas to be evacuated from the airway of subject 12. In some embodiments, the dwell time may be lengthened and/or shortened for an insufflation based on thoracic muscle compliance of subject 12, the pressure of the gas held in the lungs of subject 12, the volume of gas in the lungs of subject 12, and/or other factors.

Figure 4:
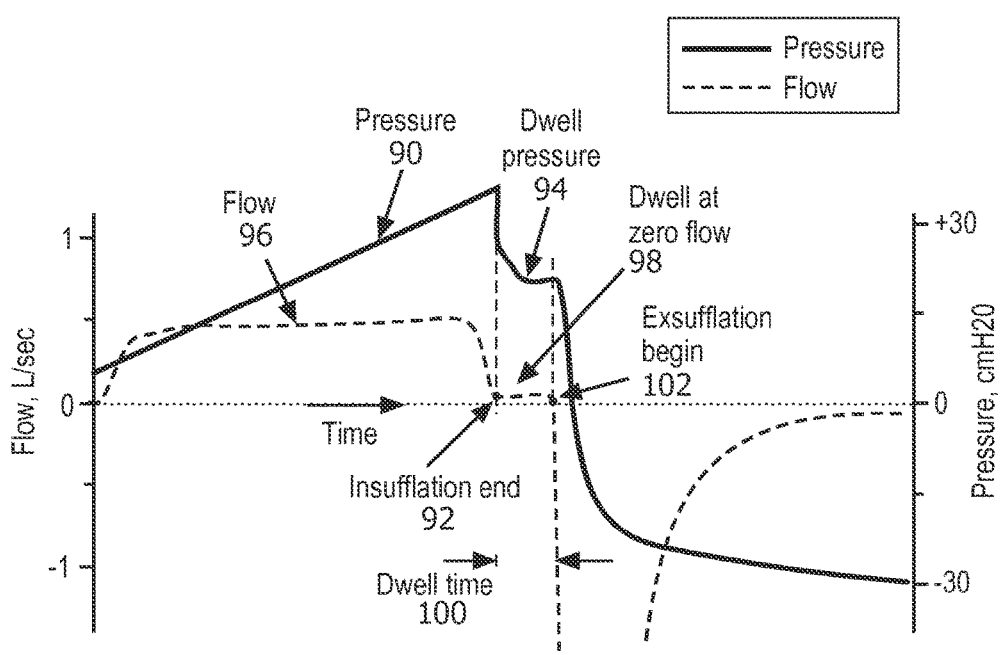
FIG. 4 is a graphical illustration of a pressure dwell generated by a pressure generator between insufflation and exsufflation of a subject.

By way of a non-limiting example, FIG. 4 is a graphical illustration (flow/pressure versus time) of a pressure dwell generated by a pressure generator between insufflation and exsufflation of a subject. The pressure 90 is steadily increased until the end of insufflation 92. At end of insufflation 92, pressure 90 is adjusted to a dwell pressure 94 to achieve a flow 96 at or near zero 98. Pressure 90 is held at dwell pressure 94 (flow 96 at or near zero) for a dwell time 100 until exsufflation begins 102.

Returning to FIG. 1, user interface 22 is configured to provide an interface between system 10 and subject 12 and/or other users through which subject 12 and/or other users may provide information to and receive information from system 10. Other users may comprise a caregiver, a doctor, a decision maker, and/or other users. This enables data, cues, results, and/or instructions and any other communicable items, collectively referred to as "information," to be communicated between a user (e.g., subject 12) and one or more of pressure generator 14, processor 20, and/or other components of system 10. Examples of interface devices suitable for inclusion in user interface 22 comprise a keypad, buttons, switches, a keyboard, knobs, levers, a display screen, a touch screen, speakers, a microphone, an indicator light, an audible alarm, a printer, a tactile feedback device, and/or other interface devices. In one embodiment, user interface 22 comprises a plurality of separate interfaces. In one embodiment, user interface 22 comprises at least one interface that is provided integrally with pressure generator 14.

It is to be understood that other communication techniques, either hard-wired or wireless, are also contemplated by the present disclosure as user interface 22. For example, the present disclosure contemplates that user interface 22 may be integrated with a removable storage interface provided by electronic storage 24. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 22 comprise, but are not limited to, an RS-232 port, RF link, an IR link, modem (telephone, cable or other). In short, any technique for communicating information with system 10 is contemplated by the present disclosure as user interface 22.

In some embodiments, electronic storage 24 comprises electronic storage media that electronically stores information. The electronic storage media of electronic storage 24 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 24 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 24 may store software algorithms, information determined by processor 20, information received via user interface 22, and/or other information that enables system 10 to function properly. Electronic storage 24 may be (in whole or in part) a separate component within system 10, or electronic storage 24 may be provided (in whole or in part) integrally with one or more other components of system 10 (e.g., user interface 22, processor 20, etc.).

Figure 5:
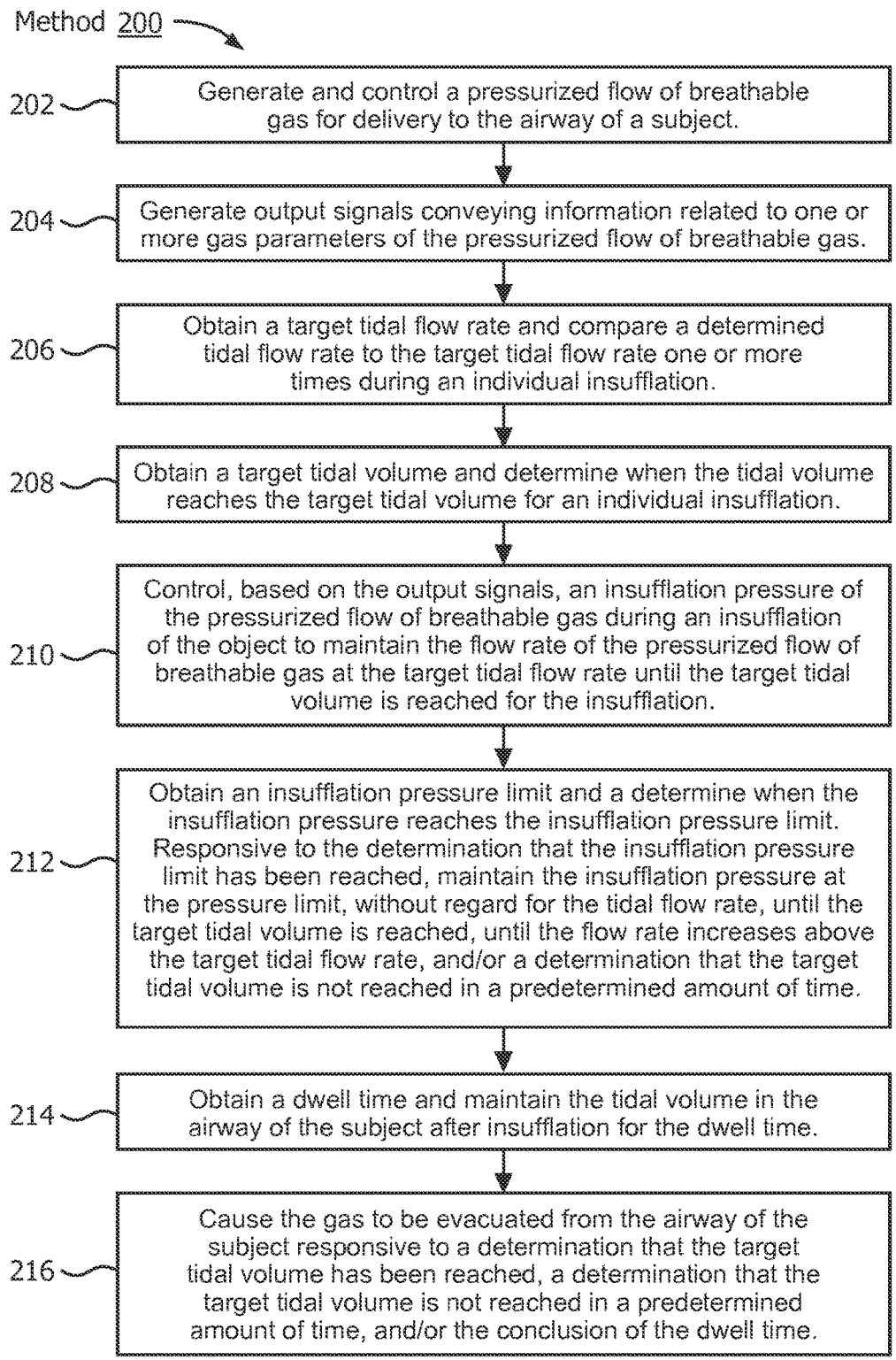
FIG. 5 illustrates a method of inexsufflating a subject.

FIG. 5 illustrates a method 200 of inexsufflating a subject. The operations of method 200 presented below are intended to be illustrative. In some embodiments, method 200 may be accomplished with one or more additional operations not described, and/or without one or more of the operations discussed. Additionally, the order in which the operations of method 200 are illustrated in FIG. 5 and described below is not intended to be limiting.

In some embodiments, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

At an operation 202, a pressurized flow of breathable gas for delivery to the airway of a subject is generated and controlled. In some embodiments, operation 202 is performed by a pressure generator the same as or similar to pressure generator 14 (shown in FIG. 1 and described herein).

At an operation 204, output signals are generated conveying information related to one or more gas parameters of the pressurized flow of breathable gas. In some embodiments, operation 204 is performed by sensors the same as or similar to sensors 18 (shown in FIG. 1 and described herein).

At an operation 206, a target tidal flow rate is obtained, the tidal flow rate is determined, and the determined tidal flow rate is compared to the target tidal flow rate one or more times during an individual insufflation. In some embodiments, operation 206 is performed by a processor module the same as or similar to target module 42 (shown in FIG. 1 and described herein).

At an operation 208, a target tidal volume is obtained, and a determination is made when the tidal volume reaches the target tidal volume for an individual insufflation. In some embodiments, operation 208 is performed by a processor module the same as or similar to target module 42 (shown in FIG. 1 and described herein).

At an operation 210, an insufflation pressure of the pressurized flow of breathable gas is controlled during an insufflation of the subject. The insufflation pressure is controlled to maintain the flow rate of the pressurized flow of breathable gas at the target tidal flow rate until the target tidal volume is reached for the insufflation. The insufflation pressure is controlled based on the output signals. In some embodiments, operation 210 is performed by a processor module and a pressure generator the same as or similar to control module 44 and pressure generator 14 (shown in FIG. 1 and described herein).

At an operation 212, an insufflation pressure limit is obtained, and a determination is made when the insufflation pressure reaches the insufflation pressure limit. Responsive to the determination that the insufflation pressure limit has been reached, the insufflation pressure is maintained at the pressure limit, without regard for tidal flow rate, until the target tidal volume is reached, until the flow rate increases above the target tidal flow, and/or a determination that the target tidal volume is not reached in a predetermined amount of time. In some embodiments, operation 212 is performed by processor modules and a pressure generator the same as or similar to limit module 46, control module 44, and pressure generator 14 (shown in FIG. 1 and described herein).

At an operation 214, a dwell time is obtained and the tidal volume in the airway of the subject is maintained after insufflation for the dwell time. In some embodiments, operation 214 is performed by processor modules and a pressure generator the same as or similar to dwell time module 48, control module 44, and pressure generator 14 (shown in FIG. 1 and described herein).

At an operation 216, the gas is evacuated from the airway of the subject responsive to a determination that the target tidal volume has been reached, a determination that the target tidal volume is not reached in a predetermined amount of time, and/or the conclusion of the dwell time. In some embodiments, operation 216 is performed by a pressure generator the same as pressure generator 14 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to inexsufflate a subject, the system comprising:
   a pressure generator configured to generate and control delivery of a pressurized flow of breathable gas to an airway of the subject;
   one or more sensors configured to generate output signals conveying information related to one or more gas parameters of the pressurized flow of breathable gas; and
   one or more processors configured by machine-readable instructions to:
      determine a target tidal flow rate, a target tidal volume, and an insufflation pressure limit based on the output signals and information related to previous respiration by the subject;
      cause the pressure generator to steadily increase a pressure of the pressurized flow of breathable gas such that a flow rate of the pressurized flow of breathable gas is maintained at the target tidal flow rate;
      responsive to the pressure of the pressurized flow of breathable gas reaching the insufflation pressure limit, cause the pressure generator to maintain the pressure of the pressurized flow of breathable gas at the insufflation pressure limit without maintaining the flow rate at the target tidal flow rate, wherein the insufflation pressure limit is reached as a result of steadily increasing the pressure starting at a beginning of inhalation of the subject; and
      responsive to a determination that the target tidal volume is reached or a determination that the target tidal volume is not reached within a predetermined amount of time, cause the pressure generator to decrease the pressure of the pressurized flow of breathable gas to a negative exsufflation pressure to evacuate the gas from the airway of the subject.

2. The system of claim 1, wherein the one or more processors are further configured to (i) determine a dwell time and a dwell pressure, (ii) responsive to the determination that the target tidal volume is reached or the determination that the target tidal volume is not reached within the predetermined amount of time, cause the pressure generator to adjust the pressure of the pressurized flow of breathable gas to the dwell pressure such that the tidal flow rate is at or near zero during the dwell time, and (iii) responsive to the expiration of the dwell time, cause the pressure generator to evacuate the gas from the airway of the subject.

3. The system of claim 2, further comprising a user interface, wherein the one or more processors are further configured to facilitate, via the user interface, entry of information indicating one or more of a starting insufflation pressure, the target tidal flow, or the target tidal volume by the subject.

4. The system of claim 1, wherein the subject triggers the system to begin insufflation.

5. The system of claim 1, wherein the one or more processors are configured such that the predetermined amount of time is (i) determined based on the output signals and the information related to previous respiration by the subject, and (ii) adjustable during an insufflation based on one or more of a lung compliance of the subject, a maximum insufflation pressure during the insufflation, or the flow rate of the pressurized flow of breathable gas during the insufflation.

6. A method of controlling a process of inexsufflating a subject with a system, the system comprising a pressure generator, one or more sensors, and one or more processors, the method comprising:
   generating and controlling, with the pressure generator, delivery of a pressurized flow of breathable gas to an airway of the subject;
   determining, with the one or more processors, a target tidal flow rate, a target tidal volume, and an insufflation pressure limit based on the output signals and information related to previous respiration by the subject;

causing, with the one or more processors, the pressure generator to steadily increase a pressure of the pressurized flow of breathable gas such that a flow rate of the pressurized flow of breathable gas is maintained at the target tidal flow rate;

responsive to the pressure of the pressurized flow of breathable gas reaching the insufflation pressure limit, causing, with the one or more processors, the pressure generator to maintain the pressure of the pressurized flow of breathable gas at the insufflation pressure limit without maintaining the flow rate at the target tidal flow rate, wherein the insufflation pressure limit is reached as a result of steadily the pressure starting at a beginning of inhalation of the subject; and responsive to a determination that the target tidal volume is reached or a determination that the target tidal volume is not reached within a predetermined amount of time, causing, with the one or more processors, the pressure generator to decrease the pressure of the pressurized flow of breathable gas to a negative an exsufflation to evacuate the gas from the airway of the subject.

7. The method of claim 6, further comprising:
(i) determining, with the one or more processors, a dwell time and a dwell pressure, (ii) responsive to the determination that the target tidal volume is reached or the determination that the target tidal volume is not reached within the predetermined amount of time, causing, with the one or more processors, the pressure generator to adjust the pressure of the pressurized flow of breathable gas to the dwell pressure such that the tidal flow rate is at or near zero during the dwell time, and (iii) responsive to the expiration of the dwell time, causing, with the one or more processors, the pressure generator to evacuate the gas from the airway of the subject.

8. The method of claim 7, further comprising facilitating, via a user interface, entry of information indicating one or more of a starting insufflation pressure, the target tidal flow, or the target tidal volume via a user interface by the subject.

9. The method of claim 6, wherein the subject triggers the start of insufflation.

10. The method of claim 6, wherein the predetermined amount of time is (i) determined based on the output signals and the information related to previous respiration by the subject, and (ii) adjustable during an insufflation based on one or more of a lung compliance of the subject, a maximum insufflation pressure during the insufflation, or the flow rate of the pressurized flow of breathable gas during the insufflation.

11. A system configured to inexsufflate a subject, the system comprising:

means for generating and controlling delivery of a pressurized flow of breathable gas to the airway of the subject;

means for generating output signals conveying information related to one or more gas parameters of the pressurized flow of breathable gas;

means for determining a target tidal flow rate, a target tidal volume, and an insufflation pressure limit based on the output signals and information related to previous respiration by the subject;

means for causing the pressure generator to steadily increase a pressure of the pressurized flow of breathable gas such that a flow rate of the pressurized flow of breathable gas is maintained at the target tidal flow rate;

responsive to the pressure of the pressurized flow of breathable gas reaching the insufflation pressure limit, means for causing the pressure generator to maintain the pressure of the pressurized flow of breathable gas at the insufflation pressure limit without maintaining the flow rate at the target tidal flow rate, wherein the insufflation pressure limit is reached as a result of steadily increasing the pressure starting at a beginning of inhalation of the subject; and responsive to a determination that the target tidal volume is reached or a determination that the target tidal volume is not reached within a predetermined amount of time, means for causing the pressure generator to decrease the pressure of the pressurized flow of breathable gas to a negative an exsufflation to evacuate the gas from the airway of the subject.

12. The system of claim 11, further comprising:
(i) means for determining a dwell time and a dwell pressure, (ii) responsive to the determination that the target tidal volume is reached or the determination that the target tidal volume is not reached within the predetermined amount of time, means for causing the pressure generator to adjust the pressure of the pressurized flow of breathable gas to the dwell pressure such that the tidal flow rate is at or near zero during the dwell time, and (iii) responsive to the expiration of the dwell time, means for causing the pressure generator to evacuate the gas from the airway of the subject.

13. The system of claim 12, further comprising means for facilitating entry of information indicating one or more of a starting insufflation pressure, the target tidal flow, or the target tidal volume by the subject.

14. The system of claim 11, wherein the subject triggers the system to begin insufflation.

15. The system of claim 11, wherein the predetermined amount of time is (i) determined based on the output signals and the information related to previous respiration by the subject, and (ii) adjustable during an insufflation based on one or more of a lung compliance of the subject, a maximum insufflation pressure during the insufflation, or the flow rate of the pressurized flow of breathable gas during the insufflation.

* * * * *